United States Patent
Pedley

(10) Patent No.: US 6,626,179 B1
(45) Date of Patent: Sep. 30, 2003

(54) BREATHING VALVE FOR IMPROVING OXYGEN ABSORPTION

(76) Inventor: Philip Pedley, P.O. Box 1, Glen Ellen, CA (US) 95442

(*) Notice: Subject to any disclaimer, the term of this patent is extended or adjusted under 35 U.S.C. 154(b) by 25 days.

(21) Appl. No.: 09/676,133

(22) Filed: Sep. 29, 2000

(51) Int. Cl.$^7$ .............................................. A61F 11/00
(52) U.S. Cl. ................................. 128/857; 128/207.18
(58) Field of Search ................................. 128/846, 848, 128/857, 858, 207.18, 206.11, 203.22, 204.12; 606/199, 204.45; 482/13

(56) References Cited

U.S. PATENT DOCUMENTS

| | | | | |
|---|---|---|---|---|
| 2,335,936 A | * | 12/1943 | Hanlon | 128/207.18 |
| 2,672,138 A | * | 3/1954 | Carlock | 128/207.18 |
| 2,751,906 A | * | 6/1956 | Irvine | 128/148 |
| 3,424,152 A | * | 1/1969 | Kuhlman | 128/848 |
| 3,556,122 A | * | 1/1971 | Laerdal | 137/102 |
| 3,747,597 A | * | 7/1973 | Olivera | 128/140 N |
| 4,280,493 A | * | 7/1981 | Council | 128/207.18 |

* cited by examiner

*Primary Examiner*—Michael A. Brown
(74) *Attorney, Agent, or Firm*—Jack Lo

(57) ABSTRACT

The present breathing valve is comprised of a hollow tubular housing sized to fit snugly inside a nostril. The housing is provided with an external thread for screwing into the nostril. A turning tool is provided for screwing and unscrewing the housing by engaging the interior of the housing. An air flow restricting device is provided within the housing. In one embodiment, the restricting device is comprised of a constricted passage for reducing air flow and increasing air pressure within the respiratory system of the user. Oxygen absorption is improved enough by the increased air pressure to eliminate the need for supplemental oxygen for people at high altitudes, and for people with respiratory problems. In a second embodiment, the restricting device is comprised of a movable restricting device which is moved to an open position during inhale to allow free passage of air. The movable restricting device is moved to a partially closed position during exhale to restrict air flow and increase air pressure within the respiratory system of the user.

7 Claims, 2 Drawing Sheets

BREATHING VALVE FOR IMPROVING OXYGEN ABSORPTION

BACKGROUND OF THE INVENTION

1. Field of the Invention

This invention relates generally to valves.

2. Prior Art

When people go to more than about 10,000 feet above sea level, such as in unpressurized aircraft or on high mountains, the low ambient air pressure can cause shortness of breath. They must increase their breathing rate to compensate for the reduced oxygen in each breath. As the brain and muscles receive less and less oxygen at higher altitudes, mental abilities become impaired, and physical exertion becomes more and more difficult. At very high altitudes, the ambient air pressure is insufficient for many to absorb enough oxygen to survive. Some people suffer from shortness of breath even at sea level. For example, older people who have smoked their whole lives and suffer from emphysema have a reduced ability to absorb oxygen.

Since atmospheric air is only about 30% oxygen, the conventional solution is to breath 100% or pure oxygen supplied from a pressurized tank. The concentrated oxygen partially or fully compensates for reduced atmospheric pressure or the user's lessened ability to absorb oxygen. However, carrying a supplemental oxygen supply is inconvenient or impractical in many situations.

OBJECTIVES OF THE INVENTION

Accordingly, the objectives of the present breathing valve are:

- to improve oxygen absorption at all altitudes without supplemental oxygen;
- to increase tolerance for reduced atmospheric pressure at high altitudes; and
- to improve oxygen absorption of people with impaired ability to absorb oxygen.

Further objectives of the present invention will become apparent from a consideration of the drawings and ensuing description.

BRIEF SUMMARY OF THE INVENTION

The present breathing valve is comprised of a hollow tubular housing sized to fit snugly inside a nostril. The housing is provided with an external thread for screwing into the nostril. A turning tool is provided for screwing and unscrewing the housing by engaging the interior of the housing. A restricting device is provided within the housing. The restricting device is moved to an open position during inhale to allow free passage of air. The restricting device is moved to a partially closed position during exhale to restrict air flow and increase air pressure within the respiratory system of the user. Oxygen absorption is improved enough by the increased air pressure to eliminate the need for supplemental oxygen for people at high altitudes, and for people with respiratory problems.

DRAWING REFERENCE NUMERALS

| | |
|---|---|
| 10. Housing | 11. Nostril |
| 12. Thread | 13. Turning Tool |
| 14. Prongs | 15. Handle |
| 16. Stops | 17. Outer Opening |
| 18. Movable Restricting Device | 19. Annular Seat |
| 20. Flap | 21. Hole |
| 22. Movable Restricting Device | 23. Annular Seat |
| 24. Gaps | 25. Breakable Tabs |
| 26. Fins | 27. Inner Opening |
| 28. Ball | 29. Air Flow Restricting Device |
| 30. Interchangeable Tube | 31. Constricted Passage |
| 32. Flange | |

DETAILED DESCRIPTION OF THE INVENTION

Figure 1:
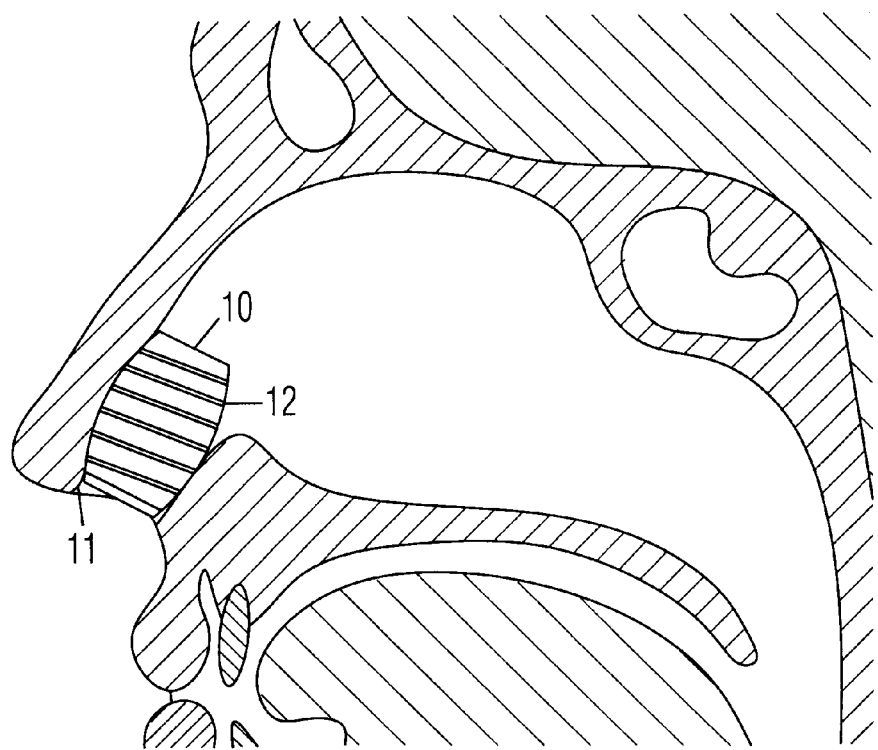
FIG. 1 is a cutaway view of a head showing the installation of the present breathing valve.

FIG. 1:

A first embodiment of the present breathing valve is shown in a side cutaway view in FIG. 1. It is comprised of a hollow tubular housing 10 sized to fit snugly inside each nostril 11 of a user. Housing 10 is provided with a shallow external thread 12 for screwing into nostril 11. Housing 10 may be provided in different sizes for fitting different people.

Figure 2:
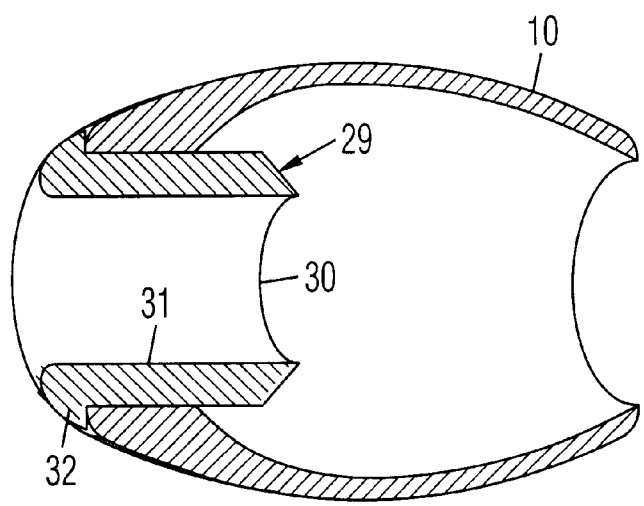
FIG. 2 is a perspective cutaway view of a first embodiment of the breathing valve.

FIG. 2:

A first embodiment of the present breathing valve is shown in a side cutaway view in FIG. 2. An air flow restricting device 29 is inserted into housing 10, and is comprised of an interchangeable hollow tube 30 with a constricted passage 31. A flange 32 is provided around an outer end of tube 30 to limit the insertion depth of restricting device 29. Constricted passage 31 has a predetermined inner diameter for restricting air passage.

The method for using the breathing valve is comprised of inhaling through the mouth for maximum oxygen intake, and exhaling through the breathing valve in the nose to reduce air flow. Air pressure within the lungs is increased due to the restricted air flow, and oxygen absorption is improved enough by the increased air pressure to eliminate the need for supplemental oxygen for people at high altitudes, and for people with respiratory problems. Different restricting devices 29 with different size constricted passages 31 may be provided to suit different people or for different altitudes.

Figure 3:
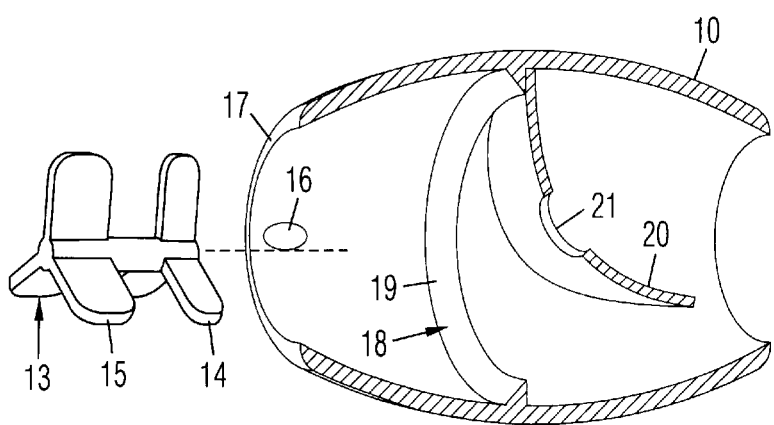
FIG. 3 is a perspective cutaway view of a second embodiment of the breathing valve during inhale.
Figure 4:
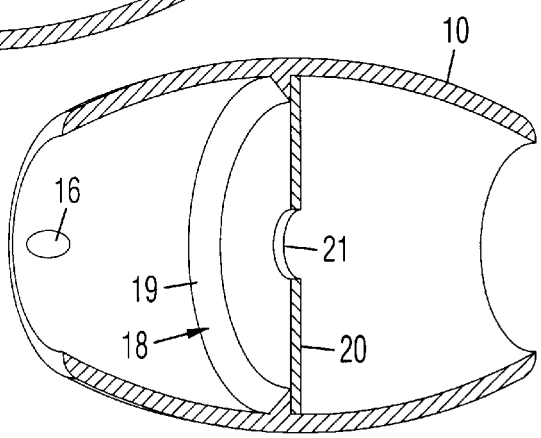
FIG. 4 is a perspective cutaway view of the breathing valve of FIG. 3 during exhale.

FIGS. 3–4:

A second embodiment of the breathing valve is shown in FIGS. 3–4. In FIG. 3, a turning tool 13 is shown for screwing and unscrewing housing 10 by engaging the interior of the housing. Tool 13 is preferably comprised of radial prongs 14 attached to a handle 15. Stops 16 are arranged in radial positions within outer opening 17 of housing 10. Prongs 14 are arranged to be inserted into outer opening 17 to engage stops 16 for turning housing 10 to screw or unscrew it from the nostril.

A movable restricting device 18 is provided within housing 10. In FIG. 3, movable restricting device 18 is automatically moved to an open position during inhale to allow free passage of air. In FIG. 4, movable restricting device 18 is moved to a partially closed position during exhale to restrict air flow and increase air pressure within the respiratory system of the user for improved oxygen absorption.

Movable restricting device 18 is preferably comprised of an annular seat 19 around an interior of housing 10. A flexible flap 20 has one end attached against an inner side of seat 19. Flap 20 is automatically forced away from seat 19 during inhale, as shown in FIG. 3, and against seat 19 during exhale, as shown in FIG. 4. A hole 21 is provided in flap 20 to pass air when flap 20 is pressed against seat 19, but at a reduced flow rate and at a higher pressure to increase oxygen absorption. The size of hole 21 may be varied to suit different individuals and to suit different environmental conditions.

Figure 5:
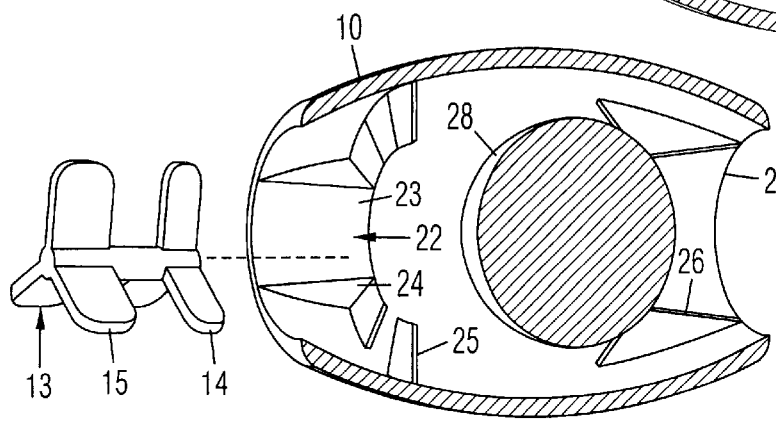
FIG. 5 is a perspective cutaway view of a third embodiment of the breathing valve during inhale.
Figure 6:
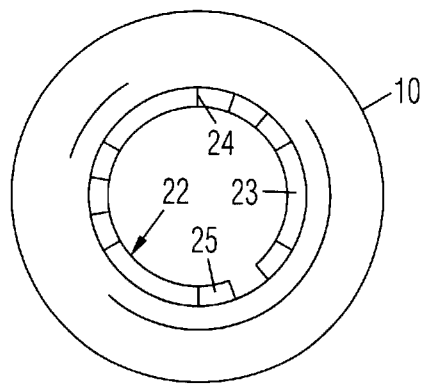
FIG. 6 is an end view of the breathing valve of FIG. 5.
Figure 7:
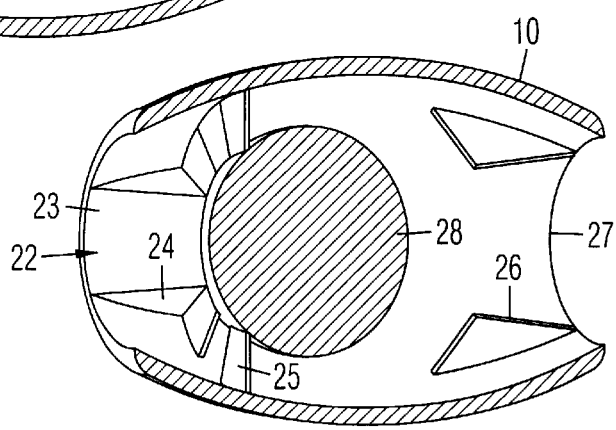
FIG. 7 is a perspective cutaway view of the breathing valve of FIG. 5 during exhale.

FIGS. 5–7:

A third embodiment of the breathing valve is shown in FIGS. 5–7. A movable restricting device 22 is provided within housing 10, and is preferably comprised of a segmented annular seat 23 around an interior of housing 10. Segmented seat 23 is provided with gaps 24 which are filled by breakable tabs 25 for passing air during exhale. A selectable number of tabs 25 may be broken away to adjust the exhale air flow and pressure to suit different individuals and different environmental conditions. Longitudinal fins 26 are positioned in radial positions around the inside of an inner opening 27 of housing 10. A movable ball 28 is automatically moved against fins 26 during inhale for freely passing air, as shown in FIG. 4, and against seat 23 and tabs 25 during exhale, as shown in FIG. 6. The holes created by removed tabs 25 pass air at a reduced flow rate and at a higher pressure to increase oxygen absorption.

SUMMARY AND SCOPE

Accordingly, the present breathing valve improves oxygen absorption at all altitudes without supplemental oxygen. It increases tolerance for reduced atmospheric pressure at high altitudes. It also improves oxygen absorption of people with impaired ability to absorb oxygen.

Although the above description is specific, it should not be considered as a limitation on the scope of the invention, but only as an example of the preferred embodiment. Many variations are possible within the teachings of the invention. For example, different attachment methods, fasteners, materials, dimensions, etc. can be used unless specifically indicated otherwise. The relative positions of the elements can vary, and the shapes of the elements can vary. Therefore, the scope of the invention should be determined by the appended claims and their legal equivalents, not by the examples given.

I claim:

1. A breathing valve, comprising:
   a hollow tubular housing adapted to fit snugly inside a nostril of a person;
   a movable restricting device arranged within said housing, wherein said movable restricting device is automatically moved to an open position during inhale for freely passing air, and said movable restricting device is automatically moved to a partially closed position during exhale to define a reduced area for passing air at a reduced flow rate and increasing air pressure within a respiratory system of said person, thereby increasing oxygen absorption; and
   an external thread around said housing for screwing into said nostril.

2. A breathing valve, comprising:
   a hollow tubular housing adapted to fit snugly inside a nostril of a person; and
   an air flow restricting device arranged within said housing, wherein said restricting device is automatically moved to an open position during inhale for freely passing air, and said restricting device is automatically moved to a partially closed position during exhale for passing air at a reduced flow rate and increasing air pressure within a respiratory system of said person, thereby increasing oxygen absorption;
   wherein said restricting device is comprised of:
   an annular seat around an interior of said housing;
   a flexible flap with one end attached against an inner side of said seat, wherein said flap is automatically forced away from said seat during inhale for freely passing air, and against said seat during exhale; and
   a hole arranged in said flap to pass air when said flap is forced against said seat during exhale, but at a reduced flow rate and at a higher pressure to increase oxygen absorption.

3. The breathing valve of claim 2, further including an external thread around said housing for screwing into said nostril.

4. The breathing valve of claim 2, further including a turning tool in combination with said housing, wherein said turning tool is comprised of radial prongs attached to a handle, said prongs are arranged to engage said interior of said housing for screwing and unscrewing housing from said nostril.

5. A breathing valve, comprising:
   a hollow tubular housing adapted to fit snugly inside a nostril of a person; and
   an air flow restricting device arranged within said housing, wherein said restricting device is automatically moved to an open position during inhale for freely passing air, and said restricting device is automatically moved to a partially closed position during exhale for passing air at a reduced flow rate and increasing air pressure within a respiratory system of said person, thereby increasing oxygen absorption;
   wherein said restricting device is comprised of:
   a segmented annular seat around an interior of said housing, said segmented seat is provided with gaps which are filled by breakable tabs, a selectable number of said tabs may be broken away to adjust the exhale air flow and pressure to suit different individuals and different environmental conditions;
   longitudinal fins positioned in spaced apart radial positions around said interior adjacent an inner end of said housing; and
   a movable ball positioned within said housing, wherein said ball is automatically moved against said fins during inhale for freely passing air, and against said segmented seat and said tabs during exhale to block air passage, except through space left by removed tabs to pass air at a reduced flow rate and at a higher pressure to increase oxygen absorption.

6. The breathing valve of claim 5, further including an external thread around said housing for screwing into said nostril.

7. The breathing valve of claim 5, further including a turning tool in combination with said housing, wherein said turning tool is comprised of radial prongs attached to a handle, said prongs are arranged to engage said interior of said housing for screwing and unscrewing housing from said nostril.

* * * * *